(12) United States Patent
Dehnhardt et al.

(10) Patent No.: US 7,342,119 B2
(45) Date of Patent: Mar. 11, 2008

(54) PROCESS FOR THE SYNTHESIS OF A CPLA$_2$ INHIBITOR

(75) Inventors: Christoph M. Dehnhardt, New York, NY (US); Sreenivasulu Megati, New City, NY (US); Ronald S. Michalak, Congers, NY (US); Panolil Raveendranath, Monroe, NY (US)

(73) Assignee: Wyeth Holdings Corporation

( * ) Notice: Subject to any disclaimer, the term of this patent is extended or adjusted under 35 U.S.C. 154(b) by 586 days.

(21) Appl. No.: 10/948,004

(22) Filed: Sep. 23, 2004

(65) Prior Publication Data

US 2005/0070723 A1    Mar. 31, 2005

Related U.S. Application Data

(60) Provisional application No. 60/507,235, filed on Sep. 30, 2003.

(51) Int. Cl.
C07D 43/02    (2006.01)
(52) U.S. Cl. .................................................. 548/455
(58) Field of Classification Search ................. 548/455
See application file for complete search history.

(56) References Cited

U.S. PATENT DOCUMENTS

| | | | |
|---|---|---|---|
| 6,635,771 B2 | 10/2003 | McKew et al. | |
| 6,797,708 B2 | 9/2004 | McKew et al. | |
| 6,891,065 B2 | 5/2005 | Wu et al. | |
| 6,984,735 B2 | 1/2006 | McKew et al. | |
| 2003/0144282 A1 | 7/2003 | Wyeth | |
| 2003/0149029 A1 | 8/2003 | McKew et al. | |
| 2003/0158405 A1 | 8/2003 | McKew et al. | |
| 2003/0166649 A1 | 9/2003 | McKew et al. | |
| 2004/0082785 A1 | 4/2004 | McKew et al. | |
| 2005/0020858 A1 | 1/2005 | Wu et al. | |
| 2005/0049296 A1 | 3/2005 | Dehnhardt et al. | |
| 2005/0148770 A1 | 7/2005 | Michalak et al. | |
| 2005/0159613 A1 | 7/2005 | Wu et al. | |
| 2006/0014759 A1 | 1/2006 | McKew et al. | |
| 2006/0041005 A1 | 2/2006 | Michalak et al. | |

OTHER PUBLICATIONS

Hoffmann et al., Fibrin-Stabilizing Factor Inhibitors. 12.5-Dibenzylaminopentylamine and Related Compounds, a New Type of FSF Inhibitors, Journal of Medicinal Chemistry (1975) vol. 18, No. 3, pp. 278-284.
Xiao et al., Regioselective Carbonylative Heteroannulation of o-Iodothiophenols with Allenes and Carbon Monoxide Catalyzed by a Palladium Complex: A Novel and Efficient Access to Thiochroman-4-one Derivatives, J. Org. Chem. (1999) vol. 64, pp. 9646-9652.
Appleton et al., A Mild and Selective C-3 Reductive Alkylation of Indoles, Tetrahedron Letters (1993) vol. 34, No. 9, pp. 1529-1532, printed in Great Britain.
Villemin et al., Palladium Homogeneous and Supported Catalysis: Synthesis of Functional Acetylenics and Cyclisation to Heterocycles, Heterocycles (1989) vol. 29, No. 7, pp. 1255-1261.
Pierce et al., Practical Asymmetric Synthesis of Efavirenz (DMP 266), and HIV-1 Reverse Transcriptase Inhibitor, J. Org. Chem. (1998) vol. 63, pp. 8536-8543.
Ezquerra et al., Efficient Reagents for the Synthesis of 5-, 7-, and 5,7-Substituted Indoles Starting from Aromatic Amines: Scope and Limitations, J. Org. Chem. 1996, vol. 61, pp. 5804-5812.
Fagnola M. et al, "Solid-Phase Synthesis of Indoles Using the Palladium-Catalysed Coupling of Alkynes with Iodoaniline Derivatives", Tetrahedron Letters,1997) vol. 38, No. 13, pp. 2307-2310.
Fujiwara et al., Nucleophilic Aromatic Substitution by Organoaluminum Reagents, Application to the Synthesis of Indoles, J. Am. Chem. Soc. (1983), vol. 105, pp. 7177-7179.

*Primary Examiner*—Kamal A. Saeed
(74) *Attorney, Agent, or Firm*—Fish & Richardson P.C.

(57) ABSTRACT

A process for making a substituted indole compound, including the steps of: reacting the compounds

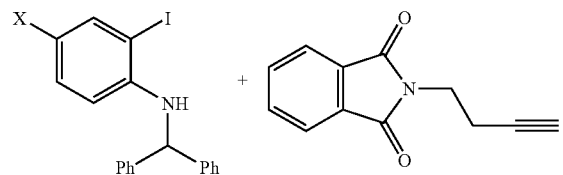

in a non-protic polar solvent in the presence of a catalyst to form the intermediate compound

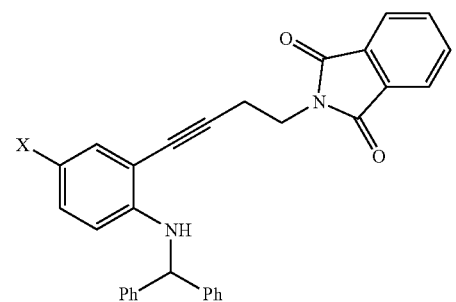

wherein Ph and X are as defined herein; and then,
heating this intermediate compound in the solvent in the presence of the catalyst to form the substituted indole compound

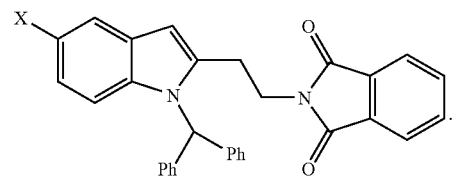

The invention also includes compounds formed by this process.

22 Claims, No Drawings

PROCESS FOR THE SYNTHESIS OF A CPLA$_2$ INHIBITOR

This application claims priority from provisional application Ser. No. 60/507,235, filed on Sep. 30, 2003 now abandoned.

FIELD OF THE INVENTION

This invention relates to a new process for the synthesis of a key intermediate for making certain compounds that inhibit cytosolic phospholipase A$_2$ (cPLA$_2$), and related compounds.

BACKGROUND OF THE INVENTION

Compounds which inhibit cytosolic phospholipase A$_2$ have been disclosed in U.S. patent application Ser. No. 10/302,636 filed Nov. 22, 2002, the disclosure of which is incorporated by reference herein. These compounds are useful for a variety of pharmaceutical purposes, including the relief of pain and inflammation. In order to bring a pharmaceutical compound to market, it is necessary to have an economically feasible process for making the compound. Often, a process that works in the laboratory is not practical from a commercial standpoint. It would be desirable to have a relatively inexpensive and efficient method for making at least some of the aforesaid compounds.

A process disclosed in U.S. patent application Ser. No. 10/302,636 for making 4-{3-[1-benzhydryl-5-chloro-2-(2-{[3,4-dichlorobenzyl)sulfonyl]amino}ethyl)-1H-indol-3-yl]propyl}benzoic acid may be summarized as follows: methyl-4-iodobenzoate is reacted with allyl alcohol to provide 4-(3-Oxo-propyl)-benzoic acid methyl ester, which is then reacted with 5-chloro-2-methylindole to yield 4-[3-(5-chloro-2-methylindol-3-yl)propyl]benzoic acid methyl ester; this product is reacted with benzhydryl bromide to produce 4-[3-(1-benzhydryl-5-chloro-2-methylindol-3-yl)propyl]benzoic acid methyl ester, which is then reacted with benzoyl peroxide to produce the 2-formyl indole; the 2 formyl indole is then reacted with nitromethane followed by Zn(Hg)/HCl to form the 2-(2-aminoethyl) indole; this amine is then reacted with [(3,4-dichlorophenyl)-methyl]sulfonyl chloride to produce 4-{3-[1-benzhydryl-5-chloro-2-(2-{[3,4-dichlorobenzyl)sulfonyl]amino}ethyl)-1H-indol-3-yl]propyl}benzoic acid methyl ester, which is then hydrolyzed to form 4-{3-[1-benzhydryl-5-chloro-2-(2-{[3,4-dichlorobenzyl)sulfonyl]amino}ethyl)-1H-indol-3-yl]propyl}benzoic acid. In this process, chromatography is used to separate some of the compounds made in the aforesaid reactions. It would be desirable to have a process for making the product that does not require the use of chromatography.

Appleton, et al., in *Tetrahedron Lett.* 1993, 34, 1529, teach reductive C-3 alkylation of 3-unsubstituted indoles to produce C-3 functionalized indoles, especially 3-(arylmethyl)indoles and 3-(heteroarylmethyl)indoles. In the reference reaction, the initial indole is reacted with an aldehyde or ketone using triethylsilane and trifluoroacetic acid.

A method for synthesizing N-but-3-ynylphthalimide is taught by Hoffmann, et al., *J. Med. Chem.*, 18(3), 278-284 (1975). In this method, phthalic acid anhydride is reacted with 4-amino-1-butyne in glacial acetic acid to produce the target compound.

Ezquerra, et al., in *J. Org. Chem.* 1998, 61, 5804-5812, disclose methods for making substituted indoles starting from aromatic amines. For example, they disclose that a 2,4-substituted aniline may be reacted with bis(pyridine) iodonium(1) tetrafluoroborate to create a 2-iodo-4,6-substituted aniline in high yield. The iodoaniline may be reacted with HC≡CS(Me)$_3$ followed by CuI in DMF to form a 5,7-substituted indole.

Xiao, et al., *J. Org. Chem.*, 64, 9646-9652 (1999), have described a preparation for 2-iodoaniline in which a 4-substituted aniline is reacted with iodine in an aqueous sodium bicarbonate solution. The authors also describe using 2-iodoaniline in the synthesis of other compounds.

Pierce, et al., in *J. Org. Chem.* 1998, 63, 8536, disclose a method for making N-benzyl anilines.

Villemin and Goussu, in *Heterocycles* 1989, 29, 1255, disclose a method and conditions for the cyclization of 2-acetyleno-anilines.

SUMMARY OF THE INVENTION

The invention comprises a process for making a substituted indole compound, said process comprising the steps of:

a) reacting the compounds

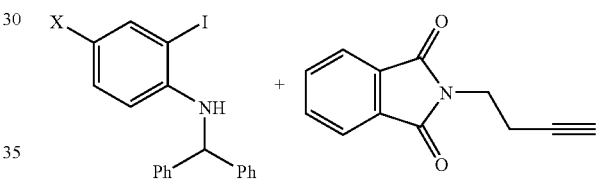

in a non-protic polar solvent in the presence of a catalyst to form the intermediate compound

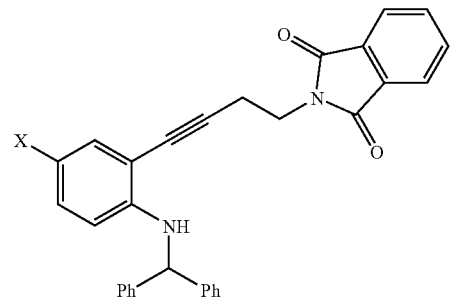

wherein Ph represents phenyl; and

X represents a moiety selected from the group consisting of H, F, Cl, Br, C$_1$-C$_{10}$-alkyl, C$_3$-C$_{10}$-cycloalkyl, and C$_6$-C$_{10}$-aryl, the alkyl moiety being optionally substituted with one or more atoms selected from F, Cl and Br, and the cycloalkyl and aryl moieties being optionally substituted with from one to three substituents selected from F, Cl, Br and C$_1$-C$_6$-alkyl; and then, b) heating said intermediate compound in the solvent in the presence of the catalyst to form the substituted indole compound

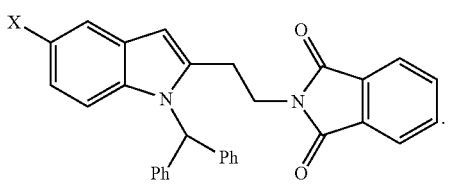

Preferably, X is F, Cl, or Br, most preferably Cl.

The process of this invention may comprise further one or more reaction shown below steps:

C) reacting said substituted indole compound with the aldehyde R—CH$_2$CH=O or with

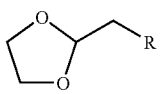

to form the tetra-substituted indole compound

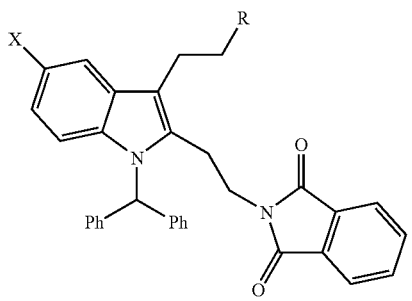

wherein

R represents C$_1$-C$_6$-alkyl, phenyl, —CH$_2$O-phenyl, —CH$_2$O—(C$_1$-C$_6$-alkyl), —CH$_2$-phen —CH$_2$CH$_2$-phenyl, or —CH$_2$-phenyl-COOZ; and Z represents H or C$_1$-C$_6$-alkyl;

d) hydrolyzing said tetra-substituted indole compound under alkali conditions to form the primary amine

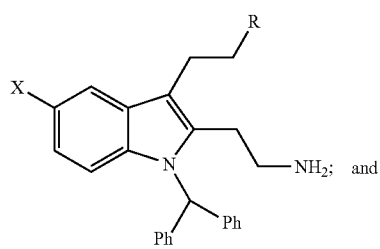

d) reacting said primary amine with

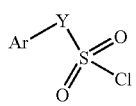

to form the compound

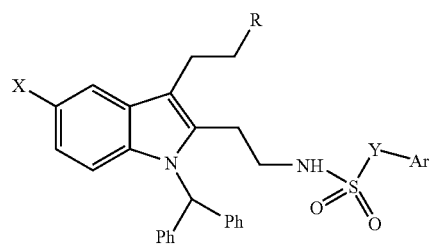

wherein Y represents (CH$_2$)$_n$—Y$_1$;

n represents an integer form 0 to 4;

Y$_1$ represents a chemical bond, S, O, S(O), S(O)$_2$, C=C, NH, N(C$_1$-C$_6$alkyl), NH—C(O), or NH(C$_1$-C$_6$alkyl)-C(O); and Ar represents a moiety selected from the group consisting of C$_1$-C$_6$ alkyl, C$_1$-C$_6$ fluorinated alkyl, C$_3$-C$_6$ cycloalkyl, tetrahydropyranyl, camphoryl, adamantyl, CN, —N(C$_1$-C$_6$ alkyl)$_2$, phenyl, pyridinyl, pyrimidinyl, furyl, thienyl, napthyl, morpholinyl, triazolyl, pyrazolyl, piperidinyl, pyrrolidinyl, imidazolyl, piperizinyl, thiazolidinyl, thiomorpholinyl, tetrazole, indole, benzoxazole, benzofuran, imidazolidine-2-thione, 7,7,dimethyl-bicyclo[2.2.1]heptan-2-one and pyrrolyl groups, each optionally substituted by from 1 to 3 substituents independently selected from the group consisting of halogen, —CN, —CHO, —CF$_3$, OCF$_3$, —OH, —C$_1$-C$_6$ alkyl, C$_1$-C$_6$ alkoxy, —NH$_2$, —N(C$_1$-C$_6$)$_2$, —NH(C$_1$-C$_6$), —N—C(O)—(C$_1$-C$_6$), —NO$_2$, —SO$_2$(C$_1$-C$_3$ alkyl), —SO$_2$NH$_2$, —SO$_2$NH(C$_1$-C$_3$ alkyl), —SO$_2$N(C$_1$-C$_3$ alkyl)$_2$, —COOH, —CH$_2$—COOH, —CH$_2$—N(C$_1$-C$_6$ alkyl), —CH$_2$—N(C$_1$-C$_6$ alkyl)$_2$, —CH$_2$—NH$_2$, pyridine,

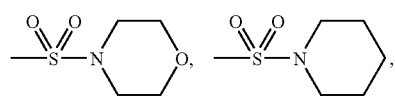

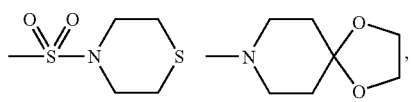

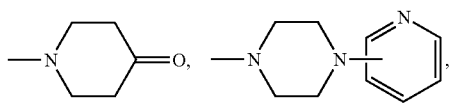

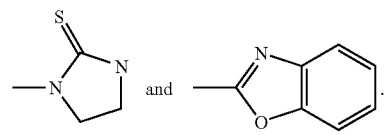

In the process of this invention, the substituted phenyl reactant may be made by the process:

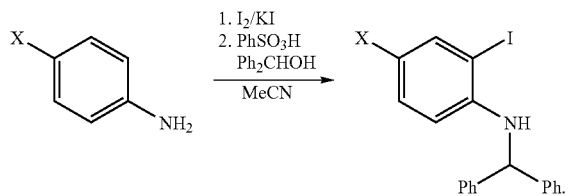

This invention further comprises novel intermediate compounds and other novel compounds created in the process of this invention, especially benzhydryl-(4-chloro-2-iodo-phenyl)-amine, 2-{4-[2-(benzhydryl-amino)-5-chloro-phenyl]-but-3-ynyl}-isoindole-1,3-dione, 2-[2-(1-benzhydryl-5-chloro-1H-indol-2-yl)-ethyl]-isoindole-1,3-dione, 4-(3-{1-benzhydryl-5-chloro-2-[2-(1,3-dioxo-1,3-dihydro-isoindol-2-yl)-ethyl]-1H-indol-3-yl}-propyl)-benzoic acid ethyl ester, and 4-(3,3-bis-{1-benzhydryl-5-chloro-2-[2-(1,3-dioxo-1,3-dihydro-isoindol-2-yl)-ethyl]-1H-indol-3-yl}-propyl)-benzoic acid ethyl ester.

Many advantages and objects of the present invention will be apparent to those skilled in the art from the following detailed description and from the appended claims.

DETAILED DESCRIPTION OF THE PREFERRED EMBODIMENTS

A preferred embodiment of the present invention is illustrated below:

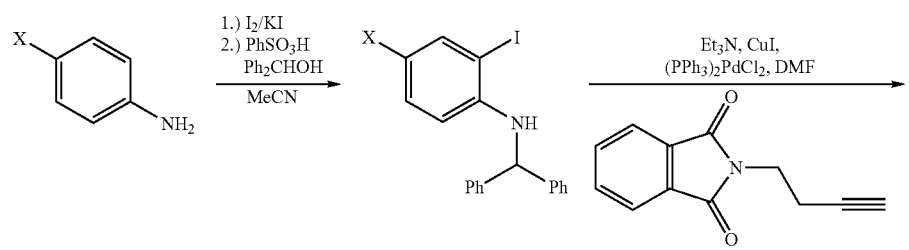

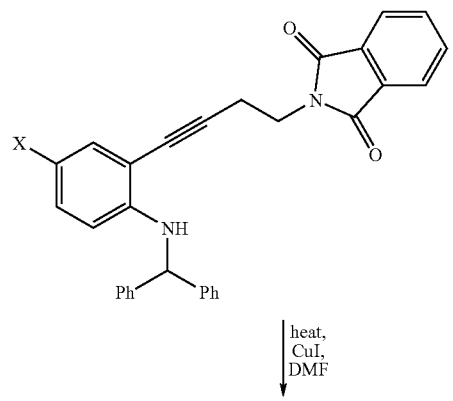

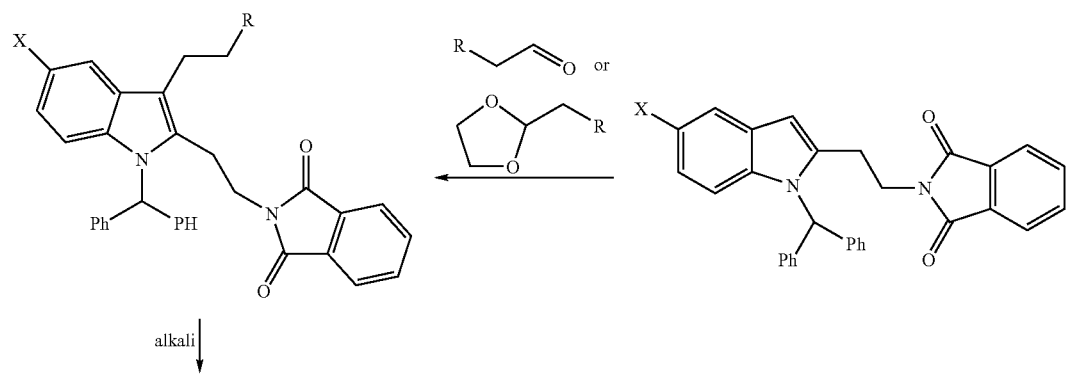

-continued

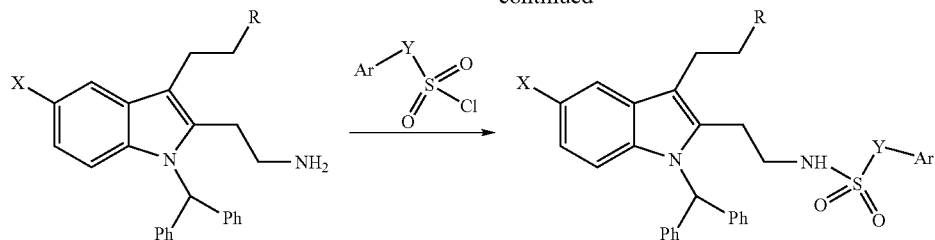

wherein
Ph represents phenyl;
Y represents $(CH_2)_n—Y_1$;
n represents an integer form 0 to 4;
$Y_1$ represents a chemical bond, S, O, S(O), S(O)$_2$, C=C, NH, N(C$_1$-C$_6$alkyl), NH—C(O), or NH(C$_1$-C$_6$alkyl)-C(O);
Ar represents a moiety selected from the group consisting of C$_1$-C$_6$ alkyl, C$_1$-C$_6$ fluorinated alkyl, C$_3$-C$_6$ cycloalkyl, tetrahydropyranyl, camphoryl, adamantyl, CN, —N(C$_1$-C$_6$ alkyl)$_2$, phenyl, pyridinyl, pyrimidinyl, furyl, thienyl, napthyl, morpholinyl, triazolyl, pyrazolyl, piperidinyl, pyrrolidinyl, imidazolyl, piperizinyl, thiazolidinyl, thiomorpholinyl, tetrazole, indole, benzoxazole, benzofuran, imidazolidine-2-thione, 7,7,dimethyl-bicyclo[2.2.1]heptan-2-one and pyrrolyl groups, each optionally substituted by from 1 to 3 substituents independently selected from the group consisting of halogen, —CN, —CHO, —CF$_3$, OCF$_3$, —OH, —C$_1$-C$_6$ alkyl, C$_1$-C$_6$ alkoxy, —NH$_2$, —N(C$_1$-C$_6$)$_2$, —NH(C$_1$-C$_6$), —N—C(O)—(C$_1$-C$_6$), —NO$_2$, —SO$_2$(C$_1$-C$_3$ alkyl), —SO$_2$NH$_2$, —SO$_2$NH(C$_1$-C$_3$ alkyl), —SO$_2$N(C$_1$-C$_3$ alkyl)$_2$, —COOH, —CH$_2$—COOH, —CH$_2$—N(C$_1$-C$_6$ alkyl), —CH$_2$—N(C$_1$-C$_6$ alkyl)$_2$, —CH$_2$—NH$_2$, pyridine,

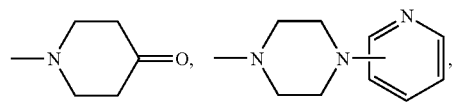

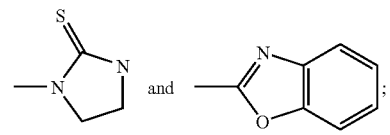

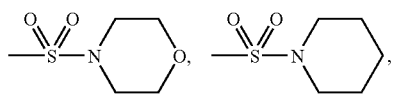

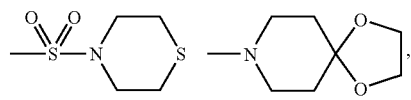

R represents C$_1$-C$_6$-alkyl, phenyl, —CH$_2$O-phenyl, —CH$_2$O—(C$_1$-C$_6$-alkyl), —CH$_2$-phen —CH$_2$CH$_2$-phenyl, or —CH$_2$-phenyl-COOZ;

Z represents H or C$_1$-C$_6$-alkyl; and

X represents a moiety selected from the group consisting of H, F, Cl, Br, C$_1$-C$_{10}$-alkyl, C$_3$-C$_{10}$-cycloalkyl, and C$_6$-C$_{10}$-aryl, the alkyl moiety being optionally substituted with one or more atoms selected from F, Cl and Br, and the cycloalkyl and aryl moieties being optionally substituted with from one to three substituents selected from F, Cl, Br and C$_1$-C$_6$-alkyl.

A highly preferred embodiment of the present invention is shown below:

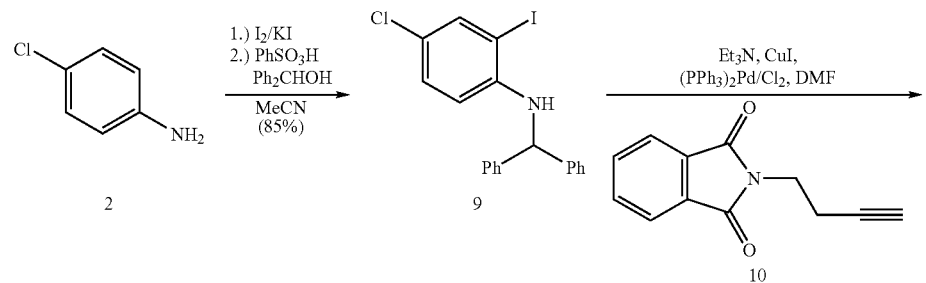

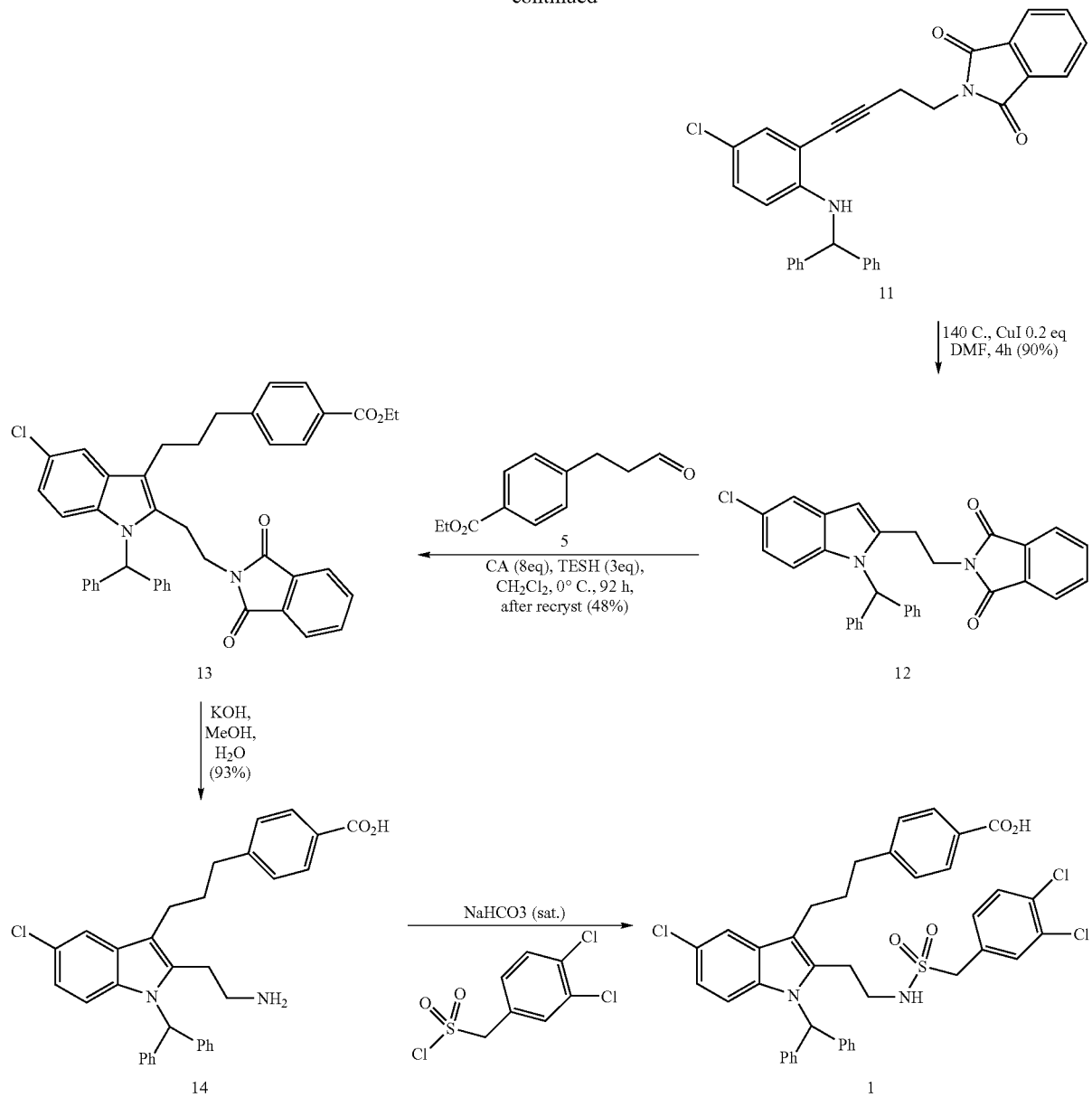

In the process of this invention, the reaction of the 4-substituted aniline 2 with diphenylmethanol produces a surprisingly high yield of the resulting intermediate compound 9, typically about 80-90% yield. The cyclization of the butynylaniline intermediate 11 to form an indole 12 also proceeds with surprisingly high yield, typically about 85-95% yield.

Advantageously, the process of the present invention does not require the use of chromatography to isolate or purify intermediate compounds.

The process of this invention represents a cost-effective, efficient, high-yielding route to cPLA$_2$ inhibitors such as 4-(3-{1-Benzhydryl-5-chloro-2-[2-(3,4-dichloro-phenyl-methanesulfonylamino)-ethyl]-1H-indol-3-yl}-propyl)-benzoic acid, and similar compounds.

In one aspect of this invention, it has been discovered that in coupling the benzhydrylaniline 9 with phthalimdo-butyne 10, the well-known Sonogashira reaction, DMF is preferable to THF to avoid high amounts of a bis-acetylenic impurity. In this embodiment, the product 11 can be precipitated from the reaction mixture after addition of water in high yield and purity.

It is also preferred to perform the cyclization to the N-benzhydryl-4-chloro-N-phthalimido-ethyl-indole 12 in DMF at about 100° C. to 150° C., and more preferably at about 140° C., under CuI catalysis, according to the general condition for the cyclisation to 2-acetyleno-anilnes described first by Vilemins and coworkers (*Hetereocycles* 1989, 29, 1255). However, it has been found that this method is surprisingly efficient for the cyclization of the diphenylmethyl substituted precursors of the present invention.

Preferably, the benzhydrylated indole 12 is reductive alkylated with an aldehyde 5, chloroacetic acid and triethylsilane to provide a 3-substituted indole 13 after crystallization from ethanol/acetonitrile. Hydrolysis under Claisen alkali condition produces the penultimate compound 14. Chloroacetic acid is an especially preferred acid in the process of this invention. Chloroacetic acid provides enough acidity for product formation without producing undesirable amounts of impurities. One impurity that can be produced in the reductive alkylation is a bis(substituted-indole) compound of the formula

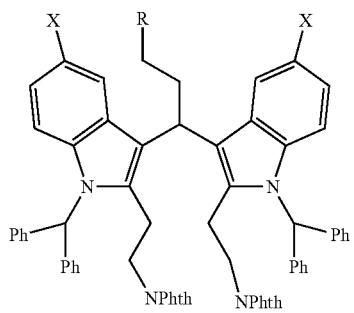

where Phth means phthaloyl. This compound can also lead to the final product, since under acidic conditions it can be cleaved to form the desired subsituted indole compound. An example of such a compound is 4-(3,3-bis-{1-benzhydryl-5-chloro-2-[2-(1,3-dioxo-1,3-dihydro-isoindol-2-yl)-ethyl]-1H-indol-3-yl}-propyl)-benzoic acid ethyl ester 15 (X=Cl; R=p-benzoic acid ethyl ester), which can be converted to the compound 13 under acidic conditions.

Those skilled in the art will appreciate that a number of non-protic polar solvents may be used in the process of this invention. The most preferred solvent for the reaction steps in which compounds 9 and 10 to produce compounds 11 and 12 is N,N-dimethylformamide (DMF). The chlorinated hydrocarbons, such as methylene chloride and ethylene chloride, are particularly preferred solvents in the reductive alkylation of compound 12 to form compound 13; these solvents have been found to promote complete consumption of the starting material.

In the practice of this invention, those skilled in the art will appreciate that many reducing agents may be used. Milder reducing agents, such as triethylsilane (TESH) and triphenylsilane, are preferred because they tend to provide higher yields and lower amounts of impurities.

Starting materials in the process of this invention, such as compounds 2, 5, 10, and the like, can be obtained by methods well known to those skilled in the art.

The following examples are presented to illustrate certain embodiments of the present invention, but should not be construed as limiting the scope of this invention.

EXAMPLE 1

SYNTHESIS OF BENZHYDRYL-(4-CHLORO-2-IODO-PHENYL)-AMINE

To a nitrogen purged 2 L three necked flask equipped with addition funnel, overhead stirrer and reflux condenser was charged 150 g(0.591 mol) 4-Chloro-2-iodo-phenylamine, 3 g(0.018 mol, 0.03 eq) benzenesulfonic acid and 500 mL acetontrile. The mixture was warmed to 70 C and 120 g (0.652 mol, 1.1 eq) benzhydrol dissolved in 500 mL acetonitrile was added to the stirred warm solution over a period of 7.5 h. After another 4 h, LC analysis showed 95% product and 5% starting material remaining. The mixture was cooled to 25 C and 290 mL water was added dropwise over a period of 30-40 min. Stirring was continued over night at 23 C. The dark purple solid was collected by filtration, washed with 2× withMeCN/water 1/1 dried at 50 C in vacuo for 15 h to give 218.5 g (88%) product.

$^1$H NMR (300 MHz, DMSO-$d_6$): δ=5.02 (d, j=5.9 Hz, 1H), 5.78 (d, j=5.9 Hz, 1 H), 6.45 (d, j=8.9 Hz, 1H), 7.16 (dd, j=8.9, 2.4 Hz, 1H), 7.24-7.42 (m, 10H), 7.71 (d, j=2.4 Hz, 1H) ppm.

EXAMPLE 2

SYNTHESIS OF 2-{4-[2-(BENZHYDRYL-AMINO)-5-CHLORO-PHENYL]-BUT-3-YNYL}-ISOINDOLE-1,3-DIONE 5 g(11.93 mmol, 1 eq) benzhydryl-(4-chloro-2-iodo-phenyl)-amine made in Example 1 was combined with 5 mL DMF. 0.42 g(0.598 mmol, 0.05 eq) dichlorobis-(triphenylphosphine)-palladium, 0.24 g(1.26 mmol, 0.11 eq) copper iodide and 1.8 g (17.58 mmol, 1.5 eq) triethylamine were added. The mixture was stirred at 25 C and 2.72 g (13.65 mmol, 1.14 eq) 2-but-3-ynyl-isoindole-1,3-dione was added in one portion. The mixture warmed to 40 C and was cooled back to room temperature. It became semi-solid after 2 h; an LC showed that at this time the reaction was complete. The mixture was diluted with 10 mL DMF and then 5 mL water was added slowly. Stirring was continued until solids precipitated. The vessel was cooled to 0-5 C and stirred at this temperature for 30 min. The resulting solid was collected by filtration and washed with 10 mL DMF/water 2:1 and 2×10 mL MeOH. The 8.78 g wet solid was dried at 40 C in vacuo for 14 h to obtain 5.55 g product (95%) with 95% purity.

$^1$H NMR (300 MHz, DMSO-$d_6$): δ=2.87 (t, j=6.6 Hz, 2H), 3.82 (t, j=6.6 Hz, 2(d, j=6.6 Hz, 1H), 5.74 (d, j=6.6 Hz, 1H), 6.45 (d, j=8.5 Hz, 1H), 7.06 (m, 2H), 7.24-7.37(m, 10H), 7.84-7.91 (m, 6H) ppm.

EXAMPLE 3

SYNTHESIS OF 2-[2-(1-BENZHYDRYL-5-CHLORO-1H—INDOL-2-YL)-ETHYL]-ISOINDOLE-1,3-DIONE

To a solution of 2-{4-[2-(Benzhydryl-amino)-5-chloro-phenyl]-but-3-ynyl}-isoindole-1,3-dione made in Example 2 (13.1 g, 26.7 mmol) in dimethylformamide (65 ml) at ambient temperature was added copper iodide (1.02 g, 5.3 mmol). The reaction mixture suspension was heated at 120 C for 16 h. Then it was heated at 140 C for 4 h. The reaction mixture was filtered at 60° C. Water (200 ml) was added to the filtrate. The product was collected after filtration and washing with water (20 ml×4). Drying the product in vacuo at 60° C. provided an off-white solid product, 2-[2-(1-Benzhydryl-5-chloro-1H-indol-2-yl)-ethyl]-isoindole-1,3-dione (12.5 g, yield 95%). HPLC (area %): 97.3%

$^1$H NMR (300 MHz, DMSO-$d_6$): δ=3.11 (t, 2H, J=7.0 Hz), 3.90 (t, 2H, J=7.0 Hz), 6.36 (s, 1H), 6.53 (d, 1H, J=8.9 Hz), 6.80 (dd, 1H, J=8.9, 2.1 Hz), 7.14 (m, 4H), 7.20 (s, 1H), 7.34 (m, 6H), 7.47 (d, 1H, J=2.1 Hz), 7.85 (m, 4H).

EXAMPLE 4

SYNTHESIS OF 4-(3-{1-BENZHYDRYL-5-CHLORO-2-[2-(1,3-DIOXO-1,3-DIHYDRO-ISOINDOL-2-YL)-ETHYL]-1H-INDOL-3-YL}-PROPYL)-BENZOIC ACID ETHYL ESTER 4.91 g (10.0 mmol, 1 eq) 2-[2-(1-Benzhydryl-5-chloro-1H-indol-2-yl)-ethyl]-isoindole-1,3-dione made according to Example 3 was suspended in 50 mL $CH_2Cl_2$. 3.50 g (30.0 mmol, 3 eq) triethylsilane, 2.47 g (12 mmol, 1.2 eq) 4-(3-Oxo-propyl)-benzoic acid ethyl ester and chloro-acetic acid 7.56 g (80 mmol, 8 eq) were added in one portion. The mixture was heated to reflux for 92 h. LC showed less then 2% starting material at this end point. 15 mL sat. aq. $NaHCO_3$ and 10 mL water was added to the reaction mixture, and stirring was continued over a period of 16 h. 10 mL MeOH was then added and the solid was collected by filtration. 9.4 g off-white solid was dried in the oven for 3 h at 60° C. to give 6.12 g 4-(3-{1-Benzhydryl-5-chloro-2-[2-(1,3-dioxo-1,3-dihydro-isoindol-2-yl)-ethyl]-1H-indol-3-yl}-propyl)-benzoic acid ethyl ester (90% yield) with 74% purity.

3.55 g of crude material was further purified by recrystallization from 15 mL ethanol/acetonitrile (1:1) to give 1.9 g product (54% yield). The overall yield for this step was 48%.

$^1$H NMR (300 MHz, DMSO-$d_6$): δ=1.31 (t, j=7.2 Hz, 3H), 1.78 (m,2H), 2.53 (t, 2H), 2.60 (t, j=7.6 Hz, 2H), 3.05 (t, j=6.9 Hz, 2H), 3.76 (t, j=6.9 Hz, 2H), 4.29 (q, j=7.2 Hz, 2H), 6.43 (d, j=8.9 Hz, 1H), 6.78 (dd, j=2.1,8.9 Hz, 1H), 7.18-7.24 (m, 7H), 7.35-7.41 (m, 6H), 7.42 (d, j=2.1 Hz, 1H), 7.79-7.86 (m, 6H) ppm.

EXAMPLE 5

SYNTHESIS OF 4-(3,3-BIS-{1-BENZHYDRYL-5-CHLORO-2-[2-(1,3-DIOXO-1,3-DIHYDRO-ISOINDOL-2-YL)-ETHYL]-1H-INDOL-3-YL}-PROPYL)-BENZOIC ACID ETHYL ESTER

Following the method of Example 4, the compound 4-(3,3-Bis-{1-benzhydryl-5-chloro-2-[2-(1,3-dioxo-1,3-dihydro-isoindol-2-yl)-ethyl]-1H-indol-3-yl}-propyl)-benzoic acid ethyl ester is formed in minor amounts.

$^1$H NMR (300 MHz, DMSO-$d_6$): δ=1.29 (t, j=7.1 Hz,3H), 2.58 (s, 2H), 2.95 (m, 3.55-3.75 (m, 4H), 4.28 (q, j=7.1 Hz, 2H), 4.43 (m, 1H), 6.36 (d, j=9.0 Hz, 2H), 6.81 (dd, j=9.0 Hz, 1.9 Hz, 2H), 6.85 (d, j=6.85 Hz, 2H), 7.03-7.19 (m, 16H), 7.31-7.33 (m, 8H), 7.46 (d, j=1.9 Hz, 2H), 7.80-7.82 (m, 10H) ppm.

EXAMPLE 6

SYNTHESIS OF 4-{2-[2-(2-AMINO-ETHYL)-1-BENZHYDRYL-5-CHLORO-1H—INDOL-3-YL]-PROPYL}-BENZOIC ACID 320 mg (0.47 mmol, 1 eq) 4-(3-{1-Benzhydryl-5-chloro-2-[2-(1,3-dioxo-1,3   2-yl)-ethyl]-1H-indol-3-yl}-propyl)-benzoic acid ethyl ester made according to Example 4 was dissolved in 1 ml MeOH and 0.28 ml water, 606 mg (10.81 mmol, 20 eq) potassium hydroxide was added, and the mixture was heated to reflux for 15 h. LC showed a completed reaction at that time. The mixture was neutralized with 1 N HCl. The product formed a semi-solid which was collected after decanting the solvent. The compound was dried between two sheets of filter paper. 228 mg (93%) of solid was obtained. Co-injection with a known sample of the product, and $^1$H-NMR confirmed the structure of 4-{2-[2-(2-Amino-ethyl)-1-benzhydryl-5-chloro-1H-indol-3-yl]-propyl}-benzoic acid.

$^1$H NMR (300 MHz, DMSO-$d_6$): δ=1.83(br.m, 2H), 2.63 (br.m, 4H), 2.72(br.m, 2H), 2.93(br.m, 2H), 6.50(d, 1H), 6.75(d, 1H), 7.08(m, 5H), 7.10(br.s, 1H), 7.33(m, 5H), 7.46(br.s, 1H), 7.75(d, 2H) ppm.

Many variations of the present invention not illustrated herein will occur to those skilled in the art. The present invention is not limited to the embodiments illustrated and described herein, but encompasses all the subject matter within the scope of the appended claims.

What is claimed is:

1. A process for making a substituted indole compound, said process comprising the steps of:

a) reacting the compounds

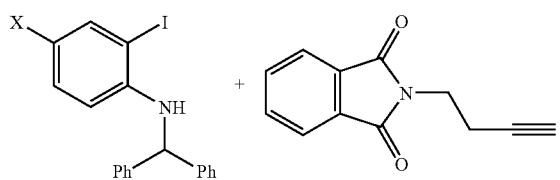

in a non-protic polar solvent in the presence of a catalyst to form the intermediate compound

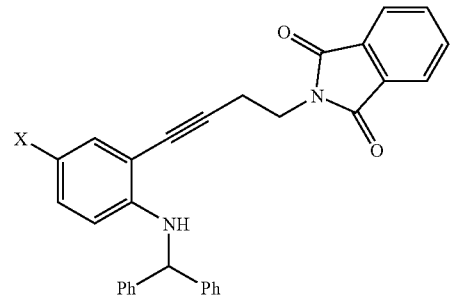

wherein Ph represents phenyl; and

X represents a moiety selected from the group consisting of H, F, Cl, Br, $C_1$-$C_{10}$-alkyl, $C_3$-$C_{10}$-cycloalkyl, and $C_6$-$C_{10}$-aryl, the alkyl moiety being optionally substituted with one or more atoms selected from F, Cl and Br, and the cycloalkyl and aryl moieties being optionally substituted with from one to three substituents selected from F, Cl, Br and $C_1$-$C_6$-alkyl; and then, b) heating said intermediate compound in the solvent in the presence of the catalyst to form the substituted indole compound

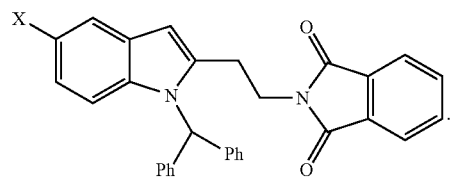

2. The process of claim 1 wherein said catalyst is selected form the group consisting of copper iodide, triethylamine, bis(triphenylphosphorus)-dichloro-palladium and combinations thereof.

3. The process of claim 1 wherein the substituted phenyl reactant is made by the process:

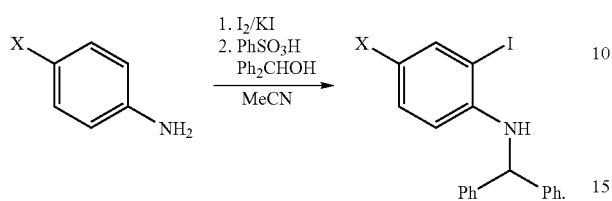

4. The process of claim 1 wherein said solvent comprises N,N-dimethylformamide and the catalyst comprises CuI.

5. The process of claim 1 further comprising reacting said substituted indole compound with the aldehyde R—CH$_2$CH=O or with

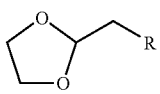

to form the tetra-substituted indole compound

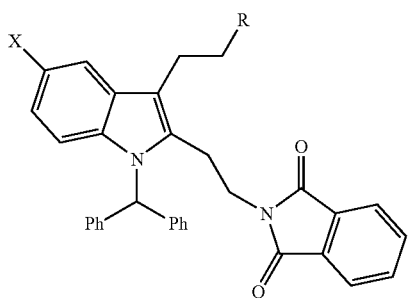

wherein
R represents C$_1$-C$_6$-alkyl, phenyl, —CH$_2$O-phenyl, —CH$_2$O-(C$_1$-C$_6$-alkyl), —CH$_2$-phenyl, —CH$_2$CH$_2$-phenyl, or —CH$_2$-phenyl-COOZ; and
Z represents H or C$_1$-C$_6$-alkyl.

6. The process of claim 5 wherein said reaction takes place in the presence of chloroacetic acid and triethylsilane.

7. The process of claim 5 further comprising hydrolyzing said tetra-substituted indole compound under alkali conditions to form the primary amine

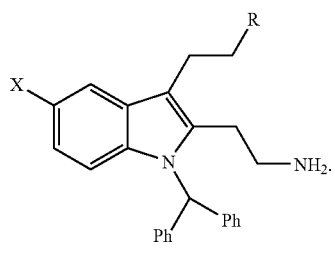

8. The process of claim 7 further comprising reacting said primary amine with

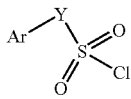

to form the compound

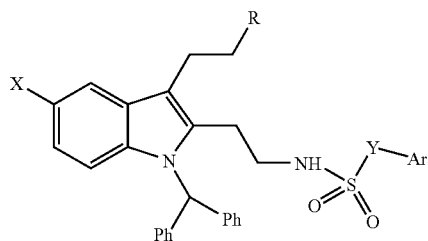

wherein Y represents (CH$_2$)$_n$-Y$_1$;
n represents an integer form 0 to 4;
Y$_1$ represents a chemical bond, S, O, S(O), S(O)$_2$, C=C, NH, N(C$_1$-C$_6$-alkyl), NH—C(O), or NH(C$_1$-C$_6$alkyl)-C(O); and
Ar represents a moiety selected from the group consisting of C$_1$-C$_6$ alkyl, C$_1$-C$_6$ fluorinated alkyl, C$_3$-C$_6$cycloalkyl, tetrahydropyranyl, camphoryl, adamantyl, CN, —N(C$_1$-C$_6$ alkyl)$_2$, phenyl, pyridinyl, pyrimidinyl, furyl, thienyl, napthyl, morpholinyl, triazolyl, pyrazolyl, piperidinyl, pyrrolidinyl, imidazolyl, piperizinyl, thiazolidinyl, thiomorpholinyl, tetrazolyl, indolyl, benzoxazolyl, benzofuranyl, imidazolidine-2-thionyl, 7,7,dimethvl-bicyclor[2.2.1]heptan-2-onyl and pyrrolyl, each optionally substituted by from 1 to 3 substituents independently selected from the group consisting of halogen, —CN, —CHO, CF$_3$, —OCF$_3$, —OH, C$_1$-C$_6$ alkyl, C$_1$-C$_6$ alkoxy, —NH$_2$, —N(C$_1$-C$_6$ alkyl)$_2$, —NH(C$_1$-C$_6$alkyl), —NH—C(O)-(C$_1$-C$_6$ alkyl), —NO$_2$, —SO$_2$(C$_1$-C$_3$ alkyl), —SO$_2$NH$_2$, —SO$_2$NH(C$_1$-C$_3$alkyl), —SO$_2$N(C$_1$-C$_3$ alkyl)$_2$, —COOH, —CH$_2$—COOH, —CH$_2$—NH(C$_1$-C$_6$alkyl), —CH$_2$-N(C$_1$-C$_6$)$_2$, —CH$_2$-NH$_2$, pyridinyl,

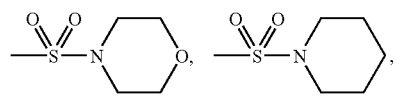

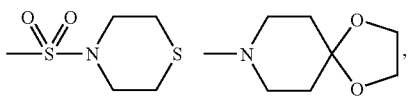

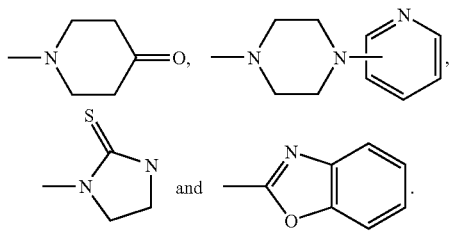

9. A process for making the compound

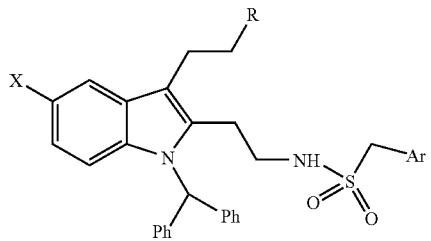

comprising the step of reacting the compounds

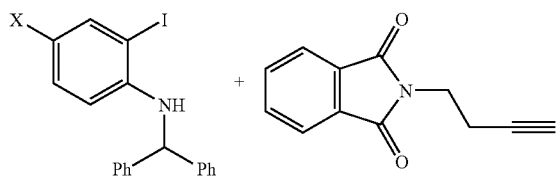

in a non-protic solvent in the presence of a catalyst to form the intermediate compound

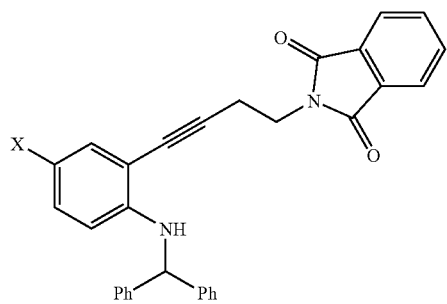

wherein Ar represents phenyl optionally substituted with one to three halogen atoms;

R represents $C_1$-$C_6$-alkyl, phenyl, —$CH_2O$-phenyl, —$CH_2O$-($C_1$-$C_6$-alkyl), -$CH_2$-phenyl, —$CH_2CH_2$-phenyl, or —$CH_2$-phenyl—COOZ;

Z represents H or $C_1$-$C_6$-alkyl;

Ph represents phenyl; and

X represents a moiety selected from the group consisting of H, F, Cl, Br, $C_1$-$C_{10}$-alkyl, $C_3$-$C_{10}$-cycloalkyl, and $C_6$-$C_{10}$-aryl, the alkyl moiety being optionally substituted with one or more atoms independently selected from F, Cl and Br, and the cycloalkyl and aryl moieties being optionally substituted with from one to three substituents independently selected from F, Cl, Br and $C_1$-$C_6$-alkyl; and then, heating said intermediate compound in the solvent in the presence of the catalyst to form the substituted indole compound

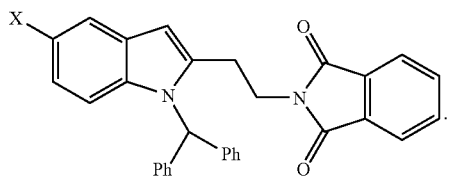

10. The process of claim 9 wherein said catalyst comprises copper iodide and the solvent comprises N,N-dimethylformamide.

11. The process of claim 10 wherein X is F, Cl or Br; R is -$CH_2$-phenyl, -$CH_2CH_2$-phenyl, or -$CH_2$-phenyl-COOZ; and Z is H or $C_1$-$C_6$-alkyl.

12. The process of claim 11 wherein X is Cl, R is -$CH_2$-phenyl-COOH, and Ar is 3,4-dichlorophenyl.

13. The process of claim 8, wherein X represents Cl or Br.

14. The process of claim 8, wherein R represents -$CH_2$-phenyl-COOZ; and Z represents H or $C_1$-$C_6$-alkyl.

15. The process of claim 8, wherein $Y_1$ represents a chemical bond.

16. The process of claim 8, wherein Ar represents phenyl optionally substituted by from 1 to 3 substituents independently selected from the group consisting of halogen, —CN, —CHO, —$CF_3$, $OCF_3$, —OH, $C_1$-$C_6$alkyl, $C_1$-$C_6$alkoxy, —$NH_2$, —N($C_1$-$C_6$-alkyl)$_2$, NH($C_1$-$C_6$-alkyl), —NH-C(O)-($C_1$-$C_6$-alkyl), —$NO_2$, —$SO_2$($C_1$-$C_3$alkyl), —$SO_2NH_2$, -$SO_2$NH($C_1$-$C_3$alkyl), -$SO_2$N($C_1$-$C_3$alkyl)$_2$, -COOH, -$CH_2$-COOH, -$CH_2$-NH($C_1$-$C_6$alkyl), -$CH_2$—N($C_1$-$C_6$ alkyl)$_2$, -$CH_2$-$NH_2$, pyridinyl,

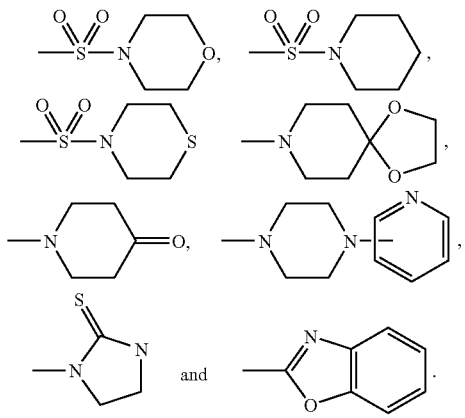

17. The process of claim 8, wherein Ar represents phenyl optionally substituted by from 1 to 3 substituents independently selected from the group consisting of halogen, —CN, —CHO, —$CF_3$, $OCF_3$, —OH, $C_1$-$C_6$alkyl, $C_1$-$C_6$alkoxy and —$NH_2$.

18. The process of claim 8, wherein:

X represents Cl or Br;

R represents -$CH_2$-phenyl-COOZ; and Z represents H or $C_1$-$C_6$-alkyl;

$Y_1$ represents a chemical bond; and

Ar represents phenyl optionally substituted by from 1 to 3 substituents independently selected from the group consisting of halogen, —CN, —CHO, —$CF_3$, $OCF_3$, —OH, $C_1$-$C_6$alkyl, $C_1$-$C_6$ alkoxy and —$NH_2$.

19. The process of claim 18, wherein n represents 1.

20. The process of claim 18, wherein Ar represents phenyl optionally substituted by from 1 to 3 substituents independently selected from the group consisting of halogen, —CF$_3$, OCF$_3$, —OH, C$_1$-C$_6$alkyl and C$_1$-C$_6$alkoxy.

21. The process of claim 18, wherein:
X represents Cl;
n represents 1; and
Ar represents phenyl optionally substituted by from 1 to 3 substituents independently selected from the group consisting of halogen, —CF$_3$, OCF$_3$, —OH, C$_1$-C$_6$alkyl and C$_1$-C$_6$alkoxy.

22. The process of claim 21, wherein R represents —CH$_2$-phenyl—COOH.

* * * * *